United States Patent [19]
McRae

[11] Patent Number: 5,823,972
[45] Date of Patent: Oct. 20, 1998

[54] PRESSURE TRANSDUCER BLADDER PRESSURE AND URINARY FLOW MEASUREMENT APPARATUS AND METHOD

[76] Inventor: Lorin P. McRae, P.O. Box 309, Oracle, Ariz. 85623

[21] Appl. No.: 656,944

[22] Filed: Jun. 6, 1996

[51] Int. Cl.⁶ .................................................. A61M 1/00
[52] U.S. Cl. .......................................... 600/573; 128/885
[58] Field of Search .................................. 128/885, 774, 128/669, DIG. 25; 604/347–353; 600/573, 574

[56] References Cited

U.S. PATENT DOCUMENTS

| | | | |
|---|---|---|---|
| 3,511,241 | 5/1970 | Lee | 604/352 |
| 4,343,316 | 8/1982 | Jespersen | 128/771 |
| 4,747,415 | 5/1988 | Lavoisier | 128/774 |
| 4,771,792 | 9/1988 | Seale | 128/774 |

Primary Examiner—Michael A. Brown
Attorney, Agent, or Firm—J. Winslow Young

[57] ABSTRACT

A minimally invasive bladder pressure and urinary flow measurement apparatus and method, the apparatus including a cuff configured to be removably mounted to the penis of the patient and an inflation system for selectively inflating and rapidly deflating the cuff. A pressure transducer is mounted to a catheter and inserted into the urethra to a position upstream from the cuff. A bead on the catheter helps the cuff hold the catheter in place. A urine collection and measurement system is provided to measure the volume and rate of urine discharged by the patient. The transient response also provides an indication whether a constriction of the urethra is proximal or distal.

19 Claims, 1 Drawing Sheet

PRESSURE TRANSDUCER BLADDER PRESSURE AND URINARY FLOW MEASUREMENT APPARATUS AND METHOD

BACKGROUND

1. Field of the Invention

This invention relates to apparatus for testing bladder pressure and urinary flow and, more particularly, to a novel, pressure transducer apparatus and method for testing bladder pressure and urinary flow to aid in the diagnosis and evaluation of patients with existing or potential urological disorders, primarily prostate pathology.

2. Related Applications

This application is a continuation-in-part application of my copending application for NONINVASIVE BLADDER PRESSURE AND URINE FLOW MEASUREMENT APPARATUS AND METHOD filed on even date herewith.

3. The Prior Art

The prostate is a muscular, walnut-shaped gland about an inch and a half long and resides directly below the bladder. At birth the prostate is quite small but enlarges considerably from puberty to about age 20 where it reaches what is considered to be its normal size. One of functions of the prostate is to produce a portion of the fluid that constitutes semen, the fluid that transports sperm. During orgasm the muscles of the prostate contract and force this fluid into the urethra. Since the prostate encircles the urethra it is in position to adversely affect the outflow of urine from the bladder. As a man ages, characteristic changes begin to occur in the prostate. For example, the aging prostate becomes more sensitive to smaller amounts of the male sex hormone, testosterone, leading some researchers to believe that estrogen plus aging equals a prostate easily influenced by testosterone, even when there is less testosterone in the body. In other words, the threshold for hormone influence is lowered.

At approximately age 40, the prostrate begins to enlarge with the result that anywhere from 10 to 30 percent of these men eventually will require treatment to relieve symptoms of difficult and/or restricted urination, incomplete bladder emptying or other associated pathology. Rarely does the prostate present a major problem before age 50, although certain changes may have been occurring as early as at least age 40.

Benign prostatic hypertrophy (BPH) is noncancerous enlargement of the prostate tissue. An enlargement of the prostate, whether cancerous or not, tends to restrict urine flow during the voiding process, micturition. As in other fluids, urine follows the hydrodynamic concept that in order for flow to occur, the urine must be subjected to a pressure differential, that is, internal pressure must be greater than any restrictions to flow. Upon initiation of micturition, the bladder generates an internal pressure sufficient to overcome the involuntary sphincter at the neck of the bladder and accelerate the urine toward the exterior. Once fluid motion is established, the bladder, by its contraction, continues to exert sufficient pressure on the urine to overcome all energy loss mechanisms in the urethra at a level sufficient to maintain urinary flow. The greatest impediment to flow usually lies in the tightest portion of the urethra at a segment called the flow control zone, which in the human male, lies in that region of the prostate between the bladder neck and the membranous urethra. In short, the prostate resides within and thus can adversely affect the flow of urine through this flow control zone.

Benign prostatic hypertrophy is, therefore, a prominent health issue that affects micturition. Treatment for a patient who has been evaluated to be thus obstructed can involve a range of treatment protocols ranging from watchful waiting to the use of medications and, in the more extreme cases, surgery. While other non-surgical medical treatments are receiving increased attention (laser ablation, balloon dilation, and non-traditional surgical approaches) surgery remains the principle treatment for this type of prostatic problem. Surgery for BPH, where the prostate is abnormally large but not cancerous, is typically less traumatic to the patient than cancer surgery. The instances of BPH are significantly more common than prostatic cancer. During 1990, diagnoses for BPH outnumbered those for prostate cancer in U.S. short stay, non-Federal hospitals by more than two to one. Prostate disease is expected to become more and more prevalent as longevity increases among U.S. men.

The typical surgery for benign prostate hypertrophy involves only a partial removal of prostatic tissue and is directed toward relieving bladder outlet obstruction. While surgery for BPH can be helpful to reduce problematic symptoms for patients who are truly obstructed, accurate diagnosis of patients thus obstructed is difficult so that surgical relief of prostate obstruction due to BPH has become one of the most common surgical procedures even in the absence of a good indicator of which patients will appropriately benefit.

Several studies have demonstrated that traditional clinical methods to determine objective need for prostate surgery are not conclusive in determining the severity of obstruction. Historically, clinical investigations include study of family history, evaluation of prostate size as estimated with conventional methods such as rectal palpation, prostate ultrasound, existence of residual urine, visualization of prostatic tissue, as well as other methods. These above-mentioned methods are not conclusive relating the degree of obstruction to the prostate. Notably, a review of the various forms of treatment indicate that up to 30% of the patients diagnosed as having BPH by the foregoing methods and who undergo surgery, did not receive the expected benefits. Studies indicate that approximately 30% of the patients undergoing surgery for BPH did not experience a significant reduction of volume of residual bladder urine after the operation. It was, therefore, concluded that a prostatic operation for this group could probably have been avoided.

The foregoing conclusion is particularly noteworthy in light of the associated surgical complications of incontinence (up to 1.2%) constriction of the urethra (12%), bladder neck narrowing or constriction (greater than 15%), loss of ejaculation (55%), and impotence (12%). Also, there exists the possibility of a second operation being necessary after 8 years is between 10.1% and 20.2%, depending on the type of surgery performed. Moreover, the mortality rate of between 0.1% and 9.0% suggests that the surgery cannot be viewed as a low risk or minor surgery. Therefore, it is of the greatest importance to prove objectively whether a patient has a bladder outlet obstruction due to the prostrate enlargement, or if his pathology is due to other factors such as urethra irritability, bladder limitations, or impaired capability of the muscle (the detrusor) that assists with the expulsion process. For these patients, pharmacological treatment or temporary bladder drainage by a catheter is possibly indicated.

Historically, one commonly used method to detect prostate pathology includes a digital rectal examination wherein the physician inserts a gloved and lubricated finger into the patient's rectum to palpate the prostate gland to determine if the prostate feels enlarged, hard, or bumpy. This procedure may be followed by performance of a biopsy of the prostate tissue if cancer is suspect. Blood tests also provide some indication if cancer has invaded the prostate gland by measurement of the amount of an antigen emitted by the prostate. However, it is much more difficult to determine BPH where cancer is not present or even suspect. Even though a patient is experiencing symptoms of difficultly in initiating urinary flow, decrease in volume urinary flow, or residual bladder urine after an attempt to empty, BPH is not always indicated. Other possibilities for the above stated symptoms are urethra irritability, bladder limitations, an impaired detrusor, or a secondary constriction (more distal to bladder).

Accordingly, it is important to be able to adequately evaluate bladder pressure and urinary flow, both its rate and volume. One prior art test requires the patient to void against a rotating disk flow transducer to measure flow. Measurement of cast distance is used as an indicator of bladder pressure and also as a check for restriction to flow. Flow and volume have also been determined by suprapubic puncture to measure the bladder pressure while voiding around an indwelling catheter. These prior art procedures are complex, uncomfortable, and/or do not provide sufficiently accurate data to enable the caregiver to determine the most efficacious treatment for the particular symptoms. Certain invasive methods can provide more accurate data than stream studies, artifacts can be introduced, and the tests are uncomfortable. Further, determination of a constriction to the urethra at the prostate is not conclusive simply by analysis of stream velocity alone. For example, as when there are two constrictions to flow (one proximal, one distal to the bladder), and where flow equilibrium occurs between the two constrictions, inadequate data will not enable one to quantify the constriction at the proximal location exclusively, i.e., at the prostate gland. This inaccuracy of data is due to the urine introduced at the proximal end passing the first constriction as a jet and then flow to the distal constriction where the urine is backed up, to a degree. Accordingly, if there are two constrictions, one proximal to the bladder at the prostate and one distal, determination of degree of constriction at the prostate cannot be determined with conventional catheter methods.

Importantly, risks and difficulty for prior art invasive methods are greatest for males who have a severely obstructed prostate, the very population for which objective testing would be most desirable. Another factor requiring careful consideration when dealing with BPH is the fact of the relatively recent advances in the discovery of medications that may be available for the treatment of BPH symptoms. Accordingly, there will be an even greater demand for a simple, noninvasive test that can be used to accurately evaluate the effectiveness of this treatment protocol. Further, even the benign process known in the art as "watchful waiting" could significantly benefit from a suitable, noninvasive, yet accurate, evaluation of bladder pressure and urinary flow. Finally, because of the inaccuracy of test results of these prior art methods, as well as associated expenses and risks, physicians most often make qualitative evaluations based on experience and symptom scoring, which leads to the performance of many (as high as 30%) unnecessary surgical procedures, making it neither practical nor safe to perform such procedures in a routine manner.

A recent, novel apparatus and method that has been discovered (and is the subject matter of the patent application filed on even date herewith) involves an inflatable cuff that is releasably mounted to the penis adjacent the glans. The cuff is inflated until it constricts the urethra. The patient then attempts to micturate while the pressure in the cuff is slowly released. Once the pressure in the cuff is incrementally less than the pressure exerted by patient on the bladder urine will begin to seep past the cuff. The pressure in the cuff at this juncture is presumed to be the pressure of the bladder. This initial seepage of urine also constitutes a trigger point for the rapid release of the pressure in the cuff to thereby enable the patient to void into a measurement vessel where the volume and rate of flow are determined. While this invention is a remarkable improvement over the current state of the art, it does have an inherent weakness in that it is rather difficult for the patient to maintain constant pressure on the bladder during the slow release of constrictive pressure from the cuff. However, perhaps the most problematic issue to contend with is that of determining the precise point at which urine begins to seep once the point at which the pressure in the cuff equals the pressure on the bladder. This issue becomes particularly important if one is to use this data to create a baseline for use in monitoring the prostatic health of a patient over time.

In view of the foregoing, it would be a significant advancement in the art to provide an apparatus and method that would more accurately measure bladder pressure and urinary flow. It would also be an advancement in the art to provide a bladder pressure and urinary flow apparatus and method that could be performed in a minimally invasive manner. An even further advancement in the art would be to provide a bladder pressure and urinary flow apparatus and method that would more accurately aid in determining the location of a constriction in the urethra. It would also be an advancement in the art to provide a pressure sensor that could be inserted into the urethra to a point immediately upstream of the cuff to thereby provide an accurate reading of bladder pressure. Such a novel invention is disclosed and claimed herein.

BRIEF SUMMARY AND OBJECT OF THE INVENTION

This invention is a novel bladder pressure and urinary flow measurement apparatus and method. The apparatus includes a pressure sensor, an occluding pressure cuff, a pressure dial, a bulb inflator, a release system, a rate and volume measurement system, a signal processor, a data recorder, a printer, and associated connection tubing. The method is practiced by placing the pressure cuff on the penis adjacent the glans where, upon inflation, the pressure cuff will selectively constrict the urethra. A catheter-mounted pressure transducer is inserted into the urethra to a point immediately up stream from the pressure cuff. Inflation of the pressure cuff constricts the urethra about the catheter to prevent urinary flow. The pressure transducer accurately measures bladder pressure, especially the maximum bladder pressure during an attempt to micturate. The pressure cuff is then rapidly deflated allowing the urinary flow to expel the pressure transducer and to flow freely into the collection vessel. Bladder pressure and the urinary flow rate are thus determined to provide an indication of the degree to which the prostate has obstructed the urethra thereby aiding in the diagnosis of benign prostatic hypertrophy. In the event there is a constriction in the urethra, an analysis of the transient response upon release of the pressure cuff provides a reliable indication as to the location of that constriction.

It is, therefore, a primary object of this invention to provide improvements in apparatus for the diagnosis of benign prostatic hypertrophy.

Another object of this invention is to provide improvements in the method of determining bladder function as it relates to benign prostatic hypertrophy.

Another object of this invention is to provide a bladder pressure and urinary flow apparatus that is minimally invasive.

Another object of this invention is to provide a bladder pressure and urinary flow apparatus that could be performed by persons other than surgically licensed personnel.

Another object of this invention is to provide a bladder pressure and urinary flow apparatus that would provide improvements in locating position of constriction to urinary flow.

Another object of this invention is to provide a bladder pressure sensing system that provides an accurate measurement of bladder pressure.

Another object of this invention is to provide a minimally invasive pressure sensor to determine bladder pressure.

Another object of this invention is to provide a catheter having a bead thereon to enable the catheter to be releasably retained in the urethra by the pressure cuff.

These and other objects and features of the present invention will become more readily apparent from the following description in which preferred and other embodiments of the invention have been set forth in conjunction with the accompanying drawing and appended claims.

BRIEF DESCRIPTION OF THE DRAWING

The drawing is a plan view of the novel pressure transducer bladder pressure and urinary flow measurement apparatus of this invention shown in the schematically illustrated environment of male genitalia.

DETAILED DESCRIPTION OF THE PREFERRED EMBODIMENT

Figure 1:
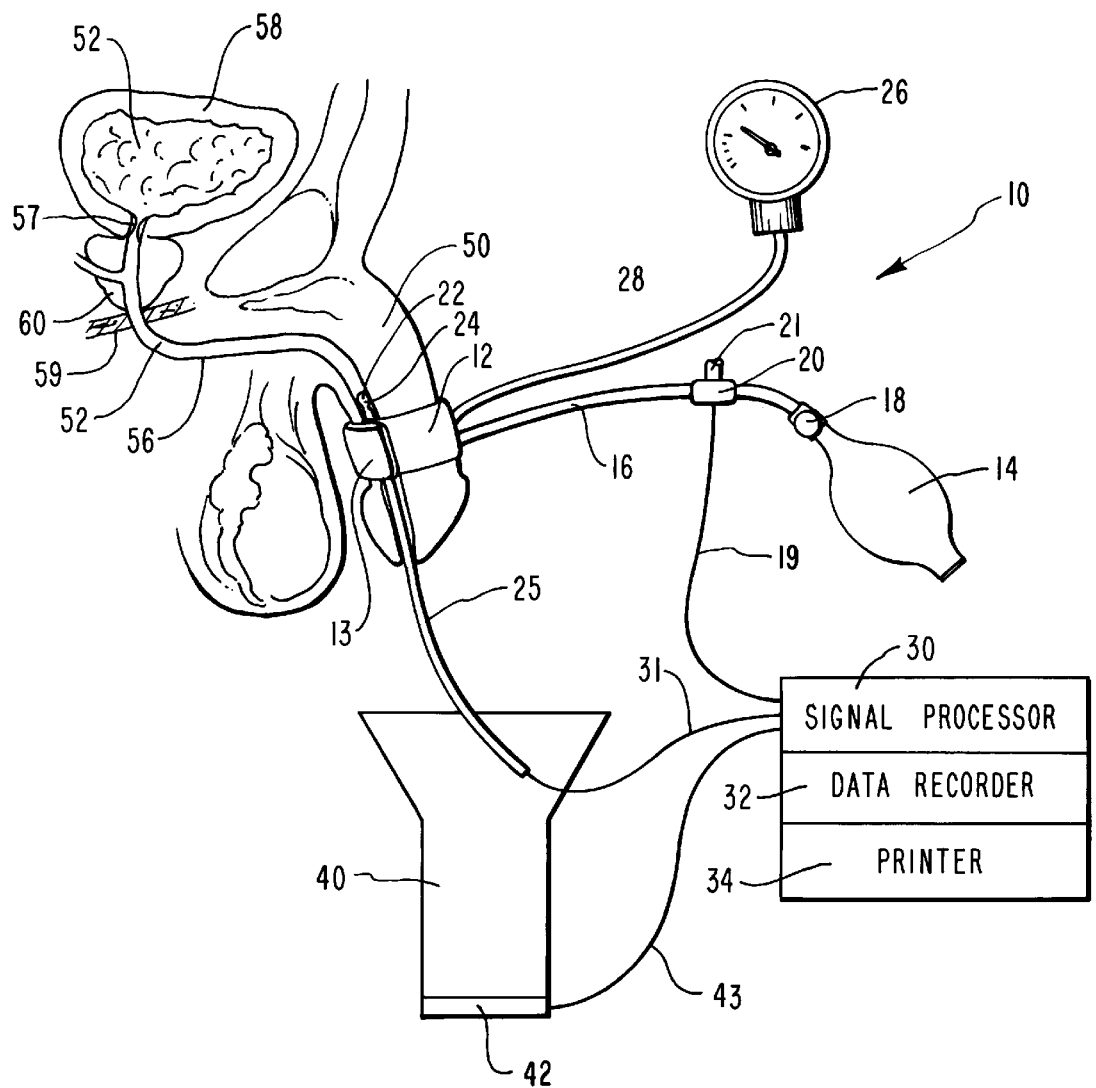

The invention is best understood from the following description with reference to the drawing wherein like parts are designated by like numerals throughout and taken in conjunction with the appended claims.

General Discussion

The underlying rationale for the pressure transducer apparatus and method of this invention for performing bladder pressure and urinary flow analysis is to (a) increase the accuracy in the diagnosis of patients experiencing urological disorders; (b) increase the accuracy of testing to determine severity of constriction to urinary flow; (c) make it possible for bladder pressure and urinary flow testing to be performed by persons other than surgically licensed personnel; and (d) provide improvements in locating the position of constriction of urinary flow.

To determine bladder pressure, a pressure transducer is inserted into the urethra and held in place by a constrictive cuff secured to the penis shaft adjacent the glans. The cuff is inflated until it constricts the urethra sufficiently to prevent the flow of urine. The patient is instructed to attempt micturition which releases the internal sphincter and exerts pressure on the bladder and urine in the urethra. This pressure is sensed by the pressure transducer which is electronically coupled to a signal processor. A bead on the end of the catheter provides a mechanism by which the constrictive cuff holds the pressure transducer in place in the urethra. Once the pressure stabilizes the signal processor causes the constrictive cuff to rapidly deflate allowing the urine in the urethra to expel the catheter. The flowing urine is then collected in a beaker where its volume and rate of flow is determined by the signal processor through a strain gauge upon which the beaker is mounted.

The minimally invasive method of measuring bladder pressure and flow of this invention also provides a more accurate determination of the location of any constriction of the urethra. Specifically, the transient flowrate waveform generated at the time of pressure release from the cuff differentiates a proximal obstruction as from the prostate from a distal obstruction such as stenosis of the meatus. Further, the novel, noninvasive bladder pressure and urinary flow measurement apparatus and method of this invention provides to the caregiver a quantitative, minimally invasive evaluation of detrusor strength and urinary flow obstruction for better evaluation of response to medication and a higher level of accurate data for use during watchful waiting for male urinary disease.

In summary, the novel pressure transducer bladder pressure measurement apparatus and method of this invention provides to the caregiver an accurate look at how well the muscles work to increase pressure on the bladder. Further, the pressure reading is not adversely affected by sphincter contraction pressure spikes whether the sphincter contraction is voluntary or involuntary. These sphincter contractions are one of the primary sources of error in obtaining bladder pressure using the constrictive cuff alone and relying on the initial flow of urine as the indicator that bladder pressure is now equal to cuff pressure. Additionally, the operator merely has to wait for the bladder pressure to stabilize before allowing the system to automatically release cuff pressure to permit urine to flow.

Although the pressure transducer is minimally invasive, it provides a superior system for obtaining bladder pressure versus a catheter inserted into the bladder. Further, urine flow studies can be commenced immediately because the catheter is expelled upon release of the constrictive force of the cuff. My studies have shown that some sort of bead arrangement is essential in order for the cuff to retain the pressure transducer in place while the bladder is being pressurized. It should also be noted that I have mounted the pressure transducer on the bead at the end of a catheter although a simple wire could replace the entire catheter. However, for ease of handling it is preferable to have the bead formed on the tip of the catheter.

Advantageously, the novel pressure transducer bladder pressure measurement of this invention provides to the caregiver a more accurate system for obtaining data about the functioning of the patient's bladder and urethra. Not only is the data more accurate, but it also provides a high level of repeatability so that as one monitors a patient over time the data baseline will remain fairly constant. Another advantage is that the present system renders itself essentially automatic so that no one need be present with the patient during the actual test. This is an important feature because I have found that many men are excessively inhibited by the presence of others during the act of micturition.

DETAILED DESCRIPTION

Referring now to the drawing, the novel bladder pressure and urinary flow measurement apparatus of this invention is shown generally as instrumentation 10 in the environment of a penis 50. Instrumentation 10 includes a cuff 12, an inflator 14, an inflation tube 16, a control valve 18, a quick release valve 20, a pressure gauge 26, and a pressure tube 28. A vent 21 on quick release valve 20 provides for the rapid deflation of cuff 12 as will be discussed more fully hereinafter. Cuff 12 is configured with an overlap section 13 having a hook and loop fastener system for releasably engaging cuff 12 about penis 50. The entire pneumatic circuitry of cuff 12, inflation tube 16, and pressure tube 28 constitutes a single pressure circuit with the pressure therein created through the use of inflator 14 and control valve 18. The pressure therein is visually displayed by pressure gauge 26. Control valve 18 allows the operator (not shown) to inflate cuff 12 to a pressure visually displayed on pressure gauge 26.

Instrumentation 10 also includes a pressure transducer 22 on a bead 24 which is formed on the end of a catheter 25. Pressure transducer 22 is electronically coupled to a signal processor 30 through a wire 31 which passes through catheter 25. Bead 24 is formed on the end of catheter 25 and provides an engagement mechanism in cooperation with cuff 12 to preclude the premature expulsion of pressure transducer 22 as will be discussed more fully hereinafter.

Signal processor 30 is electronically coupled to a data recorder 32. A printer 34 is also electronically coupled to data recorder 32 and provides a printout of the data processed through signal processor 30 and stored in data recorder 32.

A collection beaker 40 is placed below penis 50 to collect urine discharged therefrom during the practice of this invention as will be discussed more fully hereinafter. Collection beaker 40 is supported on a strain gauge 42 which, in turn, is electrically coupled to signal processor 30 by a wire 43. Signal processor 30 determines the flow rate and volume of urine collected in collection beaker 40 as sensed by strain gauge 42. This volume and flow rate information is stored in and data recorder 32.

The anatomy associated with penis 50 includes a glans 54 at the distal end of penis 50 and a urethra 56 extending the length of penis 50 at a starting point at a bladder 58 and exiting through an orifice in glans 54. A prostate 60 encircles urethra 56 adjacent bladder 58 where it can cause undue constriction of urethra 56 thereby creating problems with the discharge of urine 52 along with interference with the complete emptying of bladder 58. An involuntary, internal sphincter 57 at the junction of urethra 56 with bladder 58 releases upon contraction of bladder 58 to allow urine 52 to flow into urethra 56 from bladder 58. A voluntary, external sphincter 59 immediately distal of prostate 60 can be controlled by the patient to stop flow of urine 52.

The Method

In practicing the method of this invention the patient, for whom the functioning of bladder 58, urethra 56, and prostate 60 is to be determined, is instructed to drink approximately one liter of water commencing about one hour prior to testing. The patient or an attendant then engages cuff 12 to penis 50 adjacent glans 54. Cuff 12 is sufficiently loose at this juncture so as to not impede the flow of urine 52 through urethra 56. When the patient senses a full bladder and has the urge to micturate the patient or the attendant (not shown) inserts catheter 25 into urethra 56 until bead 24 is immediately upstream from cuff 12. This placement of bead 24 exposes pressure transducer 22 to the hydraulic circuit of urine 52. The attendant then adjusts control valve 18 and squeezes inflator 14 to cause cuff 12 to constrict penis 50 sufficiently to prevent all flow of urine 52 through urethra 56 and around catheter 25, usually at a pressure of about 230 cm of water. The patient is then instructed to urinate or, rather, attempt to micturate thus creating pressure on bladder 50 and a release of sphincters 57 and 59. The pressure on urine 52 is sensed by pressure sensor 22 and transmitted to signal processor 30 through wire 31. When the pressure is stabilized as determined by signal processor 30, quick release valve 20 is opened by a signal transmitted from signal processor 30 through a wire 19. Opening quick release valve 20 vents pressure from cuff 12 through vent 21. This rapid relaxation of cuff 12 releases bead 24 and allows the discharge of urine 52 from bladder 60 to expel catheter 25 from urethra 56. Urine 52 is discharged directly into collection beaker 40. Strain gauge 42 senses the increase in weight of collection beaker 40 from the volume of urine 52 collected therein and transmits this information to signal processor 30 through wire 43. Data recorder 32 records the total amount of urine 52 discharged into collection beaker 40 along with the rate at which urine 52 is discharged. This information along with the pressure information obtained by pressure transducer 22 provides to the medical professional (not shown) a fairly comprehensive picture of the degree to which, if any, prostate 60 impedes the outflow of urine 52 from bladder 58 and the degree to which residual urine is retained in bladder 58. Accordingly, the apparatus and method of instrumentation 10 provides a simple, minimally invasive technique for detecting the onset of BPH and for evaluating the degree of its severity. Importantly, instrumentation 10 completely avoids the insertion of any devices through urethra 56 into bladder 58 thereby effectively eliminating any significant injury to urethra 56 and also avoiding the inadvertent introduction of infectious organisms into bladder 58.

The transient response from the time of rapid release of cuff 12 until full flow of urine 52 is sensed by pressure transducer 42 provides valuable information about the location of any constriction in urethra 56. The waveform of this transient response, as sensed by signal processor 30, reveals the general location of the obstruction. For example, if the waveform has a spike in it, the obstruction is proximal whereas the absence of a spike indicates that the obstruction is distal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An apparatus for use in determining the urological condition of a male patient comprising:

a pressure cuff mountable to a penis and operable to receive pressure, said pressure causing said pressure cuff to constrict the penis to selectively control flow of urine through the urethra in the penis;

pressure sensing means for sensing urine pressure in the urethra;

pressure release means for selectively releasing said pressure in said pressure cuff;

urine collection means for collecting urine discharged from the penis;

sensing means for sensing the rate and volume of urine collected in said urine collection means; and recording means for recording said urine pressure from said pressure sensing means and said rate and said volume of urine collected as sensed by said sensing means.

2. The apparatus defined in claim 1 wherein said pressure cuff includes securement means for releasably mounting said pressure cuff to the penis.

3. The apparatus defined in claim 1 wherein said pressure means comprises a squeeze bulb and valve means for controlling the pressure from said squeeze bulb to said pressure cuff.

4. The apparatus defined in claim 1 wherein said pressure sensing means includes a pressure transducer residing in the urine.

5. The apparatus defined in claim 4 wherein said pressure sensing means includes a catheter means, said catheter means having a tip with a bead formed at said tip, said pressure transducer being mounted on said bead.

6. The apparatus defined in claim 1 wherein said pressure release means includes a quick release means for the rapid deflation of said pressure cuff.

7. The apparatus defined in claim 1 wherein said urine collection means comprises a container and said sensing means comprises a strain gauge under said container.

8. The apparatus defined in claim 1 wherein said recording means includes a print means for providing a printout of said pressure, said rate, and said volume.

9. An apparatus for determining bladder pressure and the urine output capability in a human male comprising:

a pressure cuff configured to be releasably mounted to the penis of the human male in a constrictor relationship around the penis;

pressure transducer means for measuring pressure on the urine;

inflation means for inflating in said pressure cuff to constrict the urethra in the penis;

release means for releasing said pressure cuff;

urine collection means for collecting urine passing through the urethra;

measurement means for measuring the volume and rate of flow of urine collected in said urine collection means; and recording means for recording said pressure, said volume, and said rate of flow.

10. The apparatus defined in claim 9 wherein said pressure cuff includes a strip of hook and loop fastener fabric for adjustably mounting said pressure cuff to the penis.

11. The apparatus defined in claim 9 wherein said pressure transducer means includes a catheter means for inserting said pressure transducer means into the urethra, said catheter means including a bead with said pressure transducer means mounted on said bead.

12. The apparatus defined in claim 11 wherein said release means includes a rapid release for rapidly deflating said pressure cuff.

13. The apparatus defined in claim 9 wherein said urine collection means comprises a container and said measurement means comprises a strain gauge under said container.

14. The apparatus defined in claim 9 wherein said recording means includes a printer means for providing a printout of said pressure, said rate, and said volume.

15. A method for determining bladder function in a human male patient comprising the steps of:

placing an inflatable cuff about the penis of the human male;

placing a pressure transducer in fluid communication with the urine in the urethra;

inflating said inflatable cuff to cause said inflatable cuff to prevent flow of urine through the urethra in the penis;

measuring the pressure of the urine with said pressure transducer;

deflating said inflatable cuff thereby allowing urine to flow freely under said force;

collecting the urine while measuring the rate of flow and volume of urine discharged from the bladder; and recording said pressure, said rate of flow, and said volume.

16. The method defined in claim 15 wherein said placing step includes mounting said pressure transducer on a catheter and inserting said catheter into the urethra.

17. The method defined in claim 16 wherein said mounting step includes forming a bead on an end of said catheter and placing said pressure transducer on said bead.

18. The method defined in claim 15 wherein said collecting step includes providing a vessel for collecting said urine and mounting said vessel on a strain gauge, said strain gauge measuring the volume of urine and the rate of urine in said vessel.

19. The method defined in claim 18 wherein said measuring step comprises analyzing said rate of urine for a transient response at the commencement of flow.

* * * * *